(12) United States Patent
Wolff et al.

(10) Patent No.: US 9,234,005 B2
(45) Date of Patent: Jan. 12, 2016

(54) PRODUCTS USEFUL FOR THE TREATMENT OF MALIGNANT NEOPLASMS OF THE HUMAN NERVOUS SYSTEM

(71) Applicants: Institut Pasteur, Paris (FR); Centre National de la Recherche Scientifique, Paris (FR); Universite Pierre Et Marie Curie (Paris 6), Paris (FR)

(72) Inventors: Nicolas Wolff, Paris (FR); Monique Lafon, Paris (FR); Nicolas Babault, Velaux (FR)

(73) Assignees: INSTITUT PASTEUR, Paris (FR); CENTRE NATIONAL DE LA RECHERCHE SCIENTIFIQUE, Paris (FR); UNIVERSITE PIERRE ET MARIE CURIE PARIS, Paris (FR)

( * ) Notice: Subject to any disclaimer, the term of this patent is extended or adjusted under 35 U.S.C. 154(b) by 0 days.

(21) Appl. No.: 14/350,005

(22) PCT Filed: Oct. 11, 2012

(86) PCT No.: PCT/EP2012/070200
§ 371 (c)(1),
(2) Date: Apr. 4, 2014

(87) PCT Pub. No.: WO2013/053848
PCT Pub. Date: Apr. 18, 2013

(65) Prior Publication Data
US 2014/0302123 A1    Oct. 9, 2014

(30) Foreign Application Priority Data

Oct. 11, 2011 (EP) .................................... 11306318

(51) Int. Cl.
| | |
|---|---|
| A61K 38/00 | (2006.01) |
| A61P 35/00 | (2006.01) |
| C07K 7/08 | (2006.01) |
| C07K 14/705 | (2006.01) |
| C07K 14/005 | (2006.01) |
| A61K 9/127 | (2006.01) |
| A61K 38/10 | (2006.01) |
| A61K 45/06 | (2006.01) |

(52) U.S. Cl.
CPC . *C07K 7/08* (2013.01); *A61K 9/127* (2013.01); *A61K 38/10* (2013.01); *A61K 45/06* (2013.01); *C07K 14/005* (2013.01); *C07K 14/705* (2013.01); *C12N 2760/20122* (2013.01); *C12N 2760/20133* (2013.01)

(58) Field of Classification Search
None
See application file for complete search history.

(56) References Cited

U.S. PATENT DOCUMENTS

2005/0282743 A1* 12/2005 Lu et al. .................... 514/12

FOREIGN PATENT DOCUMENTS

| EP | 2239330 | 10/2010 |
|---|---|---|
| WO | 2004045535 | 6/2004 |
| WO | 2008109010 | 9/2008 |

OTHER PUBLICATIONS

Koenig et al. Characterization of MHC Class I Restricted Cytotoxic T Cell Responses to Tax in HTLV-1 Infected Patients With Neurologic Disease. 1993. vol. 156, No. 7, pp. 3874-3883.*
Babault et al., "Peptides Targeting the PDZ Domain of PTPN4 Are Efficient Inducers of Glioblastoma Cell Death", Structure (2011), vol. 19, No. 10, pp. 1518-1524.
Prehaud et al., "Glycoprotein of Nonpathogenic Rabies Viruses Is a Key Determinant of Human Cell Apoptosis", Journal of Virology (2003), vol. 77, No. 19, pp. 10537-10547.
Prehaud et al., "Attenuation of Rabies Virulence: Takeover by the Cytoplasmic Domain of Its Envelope Protein", Science Signaling (2010), vol. 3, No. 105, ra5, pp. 1-10.
Database Accession No. UPI0001E92A28 retrieved from UniProt Consortium 2002-2014 (3 pages).
International Search Report issued in International Application No. PCT/EP2012/070200, mailed Jan. 28, 2013 (3 pages).

* cited by examiner

*Primary Examiner* — Marcela M Cordero Garcia
(74) *Attorney, Agent, or Firm* — Hunton & Williams LLP

(57) ABSTRACT

The application provides products, which may trigger pro-apoptotic or pro-death effects on neoplastic cells and/or tissues of the human nervous system, more particularly on neoplastic cells and/or tissues of the human CNS. The products of the application can be used as anti-proliferative or tumoricid agents in the treatment and/or palliation and/or prevention of neoplasms of the human nervous system, more particularly of glioblastoma or brain stem glioma. Therefore, the application also relates to compositions, such as pharmaceutical compositions or drugs, which comprise at least one of said products, as well as to the biotechnological and medical applications of said products and compositions.

20 Claims, 6 Drawing Sheets

| Peptides | Sequences | | | | | | | | | | | | Kd (μM) |
|---|---|---|---|---|---|---|---|---|---|---|---|---|---|
| | | | | | | | | -4 | -3 | -2 | -1 | 0 | |
| Cyto8-RETEV | | | | S | W | E | S | H | K | S | G | R | E | T | E | V | 1 |
| GluN2A-16 | S | N | R | R | V | Y | K | K | M | P | S | I | E | S | D | V | 42 |
| Cyto9-ESDV | | | | S | W | E | S | H | K | S | G | G | E | S | D | V | 85 |
| GluD2-13 | | | | L | N | L | G | N | D | P | D | R | G | T | S | I | 128 |
| Cyto13-att | | | | S | W | E | S | H | K | S | G | G | E | T | R | L | 157 |
| Cyto13-vir | | | | S | W | E | S | H | K | S | G | G | Q | T | R | L | 568 |
| EIRL-13 | | | | S | W | E | S | Y | R | S | G | G | E | I | R | L | 1167 |
| DARL-13 | | | | S | W | E | L | Y | K | S | E | G | D | A | R | L | 1285 |
| Cyto9-Δ | | | | S | W | E | S | H | K | S | G | G | . | . | . | . | - |

FIGURE 1

SEQUENCE LISTING

```
<160> NUMBER OF SEQ ID NOS: 17

<210> SEQ ID NO 1
<211> LENGTH: 13
<212> TYPE: PRT
<213> ORGANISM: Rabies virus

<400> SEQUENCE: 1

Ser Trp Glu Ser His Lys Ser Gly Arg Glu Thr Glu Val
1               5                   10

<210> SEQ ID NO 2
<211> LENGTH: 12
<212> TYPE: PRT
<213> ORGANISM: Rabies virus

<400> SEQUENCE: 2

Ser Trp Tyr Glu Arg Glu Thr Glu Val Ser Glu Gln
1               5                   10

<210> SEQ ID NO 3
<211> LENGTH: 9
<212> TYPE: PRT
<213> ORGANISM: Rabies virus

<400> SEQUENCE: 3

Ser Trp Glu Glu Arg Glu Thr Glu Val
1               5

<210> SEQ ID NO 4
<211> LENGTH: 11
<212> TYPE: PRT
<213> ORGANISM: Rabies virus

<400> SEQUENCE: 4

Ser Trp Ala Arg Val Ser Lys Glu Thr Pro Leu
1               5                   10

<210> SEQ ID NO 5
<211> LENGTH: 9
<212> TYPE: PRT
<213> ORGANISM: Rabies virus

<400> SEQUENCE: 5

Ser Trp Glu Arg Arg Glu Thr Glu Val
1               5

<210> SEQ ID NO 6
<211> LENGTH: 9
<212> TYPE: PRT
<213> ORGANISM: Rabies virus

<400> SEQUENCE: 6

Ser Trp Glu Glu Arg Glu Thr Glu Phe
1               5

<210> SEQ ID NO 7
<211> LENGTH: 9
<212> TYPE: PRT
```

```
<213> ORGANISM: Rabies virus

<400> SEQUENCE: 7

Ser Trp Glu Asp Arg Glu Thr Glu Val
1               5

<210> SEQ ID NO 8
<211> LENGTH: 16
<212> TYPE: PRT
<213> ORGANISM: Homo sapiens

<400> SEQUENCE: 8

Ser Asn Arg Arg Val Tyr Lys Lys Met Pro Ser Ile Glu Ser Asp Val
1               5                   10                  15

<210> SEQ ID NO 9
<211> LENGTH: 13
<212> TYPE: PRT
<213> ORGANISM: Rabies virus

<400> SEQUENCE: 9

Ser Trp Glu Ser His Lys Ser Gly Gly Glu Ser Asp Val
1               5                   10

<210> SEQ ID NO 10
<211> LENGTH: 13
<212> TYPE: PRT
<213> ORGANISM: Homo sapiens

<400> SEQUENCE: 10

Leu Asn Leu Gly Asn Asp Pro Asp Arg Gly Thr Ser Ile
1               5                   10

<210> SEQ ID NO 11
<211> LENGTH: 13
<212> TYPE: PRT
<213> ORGANISM: Rabies virus

<400> SEQUENCE: 11

Ser Trp Glu Ser His Lys Ser Gly Gly Glu Thr Arg Leu
1               5                   10

<210> SEQ ID NO 12
<211> LENGTH: 11
<212> TYPE: PRT
<213> ORGANISM: Rabies virus

<400> SEQUENCE: 12

Ser Trp Pro Asp Arg Asp Arg Glu Ser Ile Val
1               5                   10

<210> SEQ ID NO 13
<211> LENGTH: 11
<212> TYPE: PRT
<213> ORGANISM: Rabies virus

<400> SEQUENCE: 13

Ser Trp Arg Val Asp Ser Lys Glu Thr Glu Cys
1               5                   10

<210> SEQ ID NO 14
<211> LENGTH: 13
<212> TYPE: PRT
<213> ORGANISM: Rabies virus
```

-continued

```
<400> SEQUENCE: 14

Ser Trp Glu Ser His Lys Ser Gly Gly Gln Thr Arg Leu
1               5                   10

<210> SEQ ID NO 15
<211> LENGTH: 13
<212> TYPE: PRT
<213> ORGANISM: Rabies virus

<400> SEQUENCE: 15

Ser Trp Glu Ser Tyr Arg Ser Gly Gly Glu Ile Arg Leu
1               5                   10

<210> SEQ ID NO 16
<211> LENGTH: 13
<212> TYPE: PRT
<213> ORGANISM: Rabies virus

<400> SEQUENCE: 16

Ser Trp Glu Leu Tyr Lys Ser Glu Gly Asp Ala Arg Leu
1               5                   10

<210> SEQ ID NO 17
<211> LENGTH: 9
<212> TYPE: PRT
<213> ORGANISM: Rabies virus

<400> SEQUENCE: 17

Ser Trp Glu Ser His Lys Ser Gly Gly
1               5
```

PRODUCTS USEFUL FOR THE TREATMENT OF MALIGNANT NEOPLASMS OF THE HUMAN NERVOUS SYSTEM

CROSS-REFERENCE TO RELATED APPLICATIONS

This application is the national phase application of International Patent Application Number PCT/EP2012/070200, filed Oct. 11, 2012, which claims the benefit of European Patent Application Number EP 11306318.4, filed Oct. 11, 2011, the contents of each of which are hereby incorporated by reference in their entirety.

FIELD OF THE INVENTION

The application relates to products, which can be used as anti-proliferative or tumoricid agents in the treatment and/or palliation and/or prevention of neoplasms of the human nervous system.

The application also relates to means deriving from said products, such as pharmaceutical compositions, as well as to the applications of said products and means, more particularly in the medical and/or biotechnological fields.

BACKGROUND OF THE INVENTION

Tumors develop when, in a healthy organ, cells display uncontrolled growth and division beyond the normal limits and escape cell death mechanisms.

Viruses are masters for manipulating the proliferation or death of the host cell they infect, mainly by interfering with crucial endogenous interactions. Rabies virus (RABV) is a neurotropic virus, which causes fatal encephalitis in mammals. RABV has developed a particular strategy to ensure its propagation in the nervous system. Its virulence correlates with the ability of infected neurons to survive.

Virulent RABV strains have been described to preserve the integrity of the neuronal network, thereby favoring the spreading of the virulent strain within the Central Nervous System (CNS), although they have also been described to have no positive or a negative impact on neurite outgrowth, for example no positive or a negative impact on axon outgrowth of rat motoneurons in culture (Guigoni and Coulon, 2002).

Attenuation of laboratory strains in the search for candidate live anti-RABV vaccines led to the observation that RABV attenuation is linked to their ability to trigger cell death. WO 03/048198 relates to the G protein of RABV and to fragments thereof of at least 100 amino acids, which induce the disruption of the neuronal cell integrity and the formation of apoptotic bodies. WO 03/048198 describes that the effect of these apoptotic bodies is to stimulate a humoral immune response, preferably a B-dependent humoral immune response.

Préhaud et al., 2010 have described that the various partners of attenuated rabies virus strains include PTPN4, MAST2, MAST1, DLG2, MDPZ. A cell—penetrating peptide (Cyto13-att; SEQ ID NO: 11) encoding the PDZ binding site (PDZ-BS) of the attenuated ERA rabies virus strain induces cell death in the neuroblastoma cell line SK-N-SH, whereas peptides from the virulent VIR strain PDZ-BS (Cyto13-vir; SEQ ID NO: 14) or peptides lacking the last four amino acids (Cyto9-Δ; SEQ ID NO: 17) do not (Préhaud et al., 2010).

SUMMARY OF THE INVENTION

The application provides products, which may notably trigger pro-apoptotic or pro-death effects on neoplastic cells and/or tissues of the human nervous system, more particularly on neoplastic cells and/or tissues of the human CNS. The products of the application can be used as anti-proliferative or tumoricid agents in the treatment and/or palliation and/or prevention of neoplasms of the human nervous system, more particularly of glioblastoma or brain stem glioma. Therefore, the application also relates to compositions, such as pharmaceutical compositions or drugs, which comprise at least one of said products, as well as to the biotechnological and medical applications of said products and compositions.

BRIEF DESCRIPTION OF THE FIGURES

FIG. 1. Sequence alignment of some peptides and their affinity for PTPN4-PDZ. Sequence alignment of the C-termini PDZ-BS of nine peptides sorted according to their Kd value for PTPN4-PDZ as measured by NMR (Préhaud et al., 2010): Cyto8-RETEV (optimized sequence; SEQ ID NO: 1); GluN2A-16 (SEQ ID NO: 8) and GluD2-13 (SEQ ID NO: 10) encompassing the C-terminal sequences of endogenous partners of PTPN4-PDZ, GluN2A and GluD2, respectively; Cyto13-att (SEQ ID NO: 11) from the ERA-NIV RABV strain; Cyto13-vir (SEQ ID NO: 14) from the CVS-NIV RABV strain; EIRL-13 (SEQ ID NO: 15) from the CVS-B2c RABV strain; DARL-13 (SEQ ID NO: 16) from the vampire bat RABV strain; the chimeric peptide Cyto9-ESDV (SEQ ID NO: 9) encoding the PDZ-BS-RETEV$_{COOH}$ with the core of Cyto13-att; Cyto9-Δ (SEQ ID NO: 17) corresponding to Cyto13-att truncated from its PDZ-BS.

TABLE 1

Student's t test values

| | Cyto9-Δ | Cyto13-vir | Cyto13-att | Cyto9-ESDV | GluN2A-16 | Cyto8-RETEV |
|---|---|---|---|---|---|---|
| Cyto9-Δ | ND | 0.3011 | 0.0128 | 0.0042 | 0.0006 | 2.29e−08 |
| Cyto13-vir | | ND | 0.0548 | 0.0350 | 0.0106 | 1.42e−05 |
| Cyto13-att | | | ND | 0.1414 | 0.0017 | 9.71e−09 |
| Cyto9-ESDV | | | | ND | 0.0100 | 2.18e−07 |
| GluN2A-16 | | | | | ND | 0.032 |
| Cyto8-RETEV | | | | | | ND |

FIGS. 3A-3D. Structures of PTPN4-PDZ bound to Cyto13-att (SEQ ID NO: 11) and GluN2A-16 (SEQ ID NO: 8). (A) Superposition of PTPN4-PDZ bound to Cyto13-att (light green/green, B) and GluN2A-16 (light blue/blue, C). Peptides enter the PDZ binding pocket delimited by the β2-strand, α2-helix, and carboxylate-binding loop $^{526}$GRFGF$^{530}$, a conserved PDZ signature. (B) and (C) Close-up views of the PTPN4-PDZ/peptide binding sites. Important residues are shown as sticks in CPK colors. Peptides form an antiparallel β-sheet with the β2-strand via a complete set of intermolecular canonical backbone H-bonds (black dashed lines). Other intermolecular H-bonds are shown in orange dashed lines. (D) Secondary-structure elements in PTPN4-PDZ.

Figures 4A, 4B:
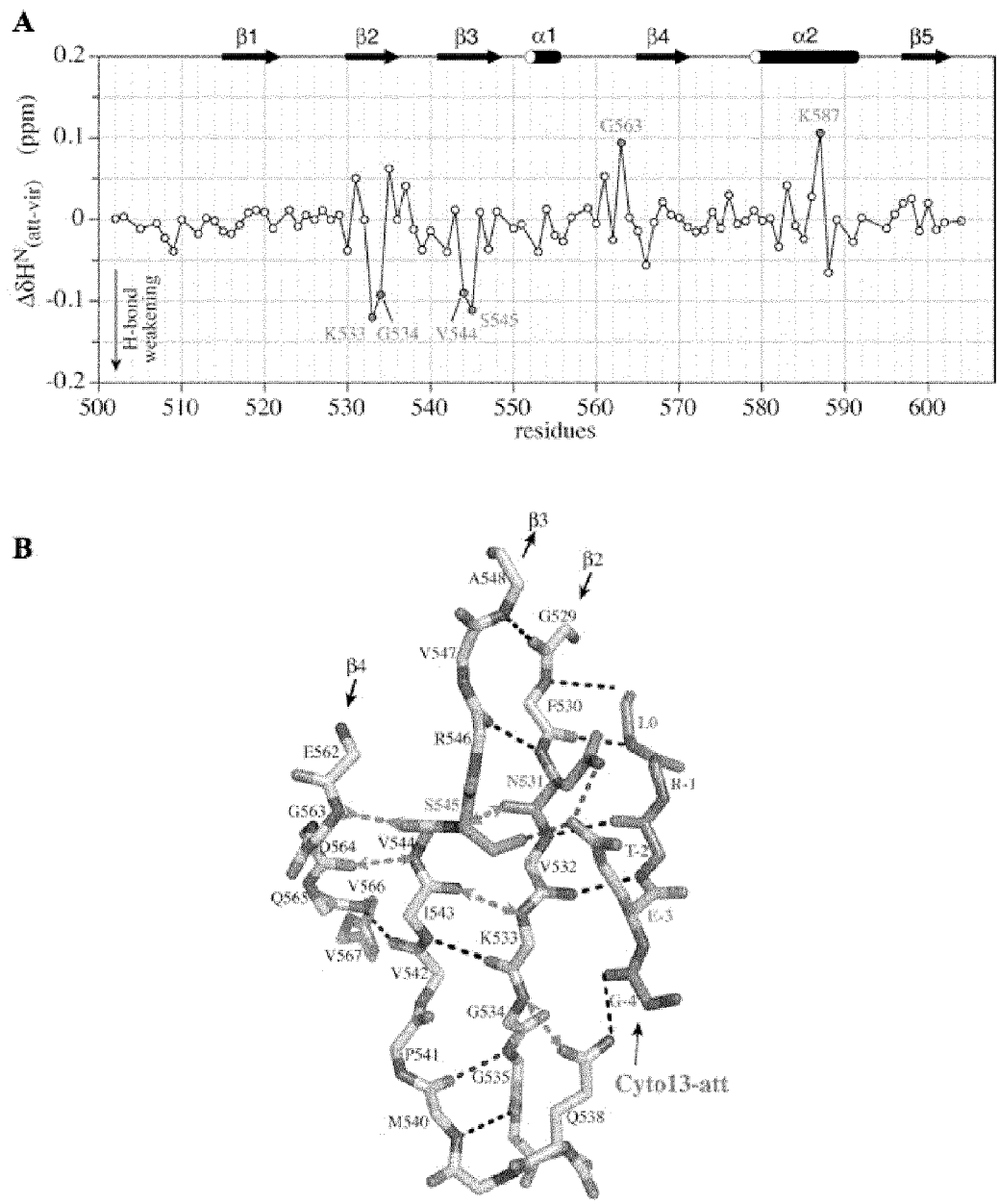

FIGS. 4A-4B. (A) Differences in PTPN4-PDZ amide proton chemical shifts between PTPN4-PDZ/Cyto13-att and PTPN4-PDZ/Cyto13-vir complexes, $\Delta\delta^{HN}=\delta^{HN}(att)-\delta^{HN}(vir)$. The residues that shifted most upfield in the PTPN4-PDZ/Cyto13-att complex are labelled in green and correspond to a weakening of the corresponding H-bonds. Likewise, downfield shifts are in magenta and correspond to strengthening. Upfield shifts of approximately 0.1 ppm correspond to H-bond lengthening of roughly 2-5 pm. Residues K533, G534, V544, S545, and G563 are located in the β-sheet formed by strands β2, β3, and β4, and K587 is located on the face of the α2 helix pointing towards the peptide. (B) Region of the PTPN4-PDZ/Cyto13-att structure showing the β-sheet formed by strands β2, β3, and β4 (light green) and the Cyto13-att peptide (green), and the corresponding H-bond network (black and red dotted lines). Nitrogen and oxygen atoms are in blue and red, respectively. As monitored by the changes in amide proton chemical shifts, the H-bonds depicted by green dotted lines are weakened in the PTPN4-PDZ/Cyto13-att complex compared to the PTPN4-PDZ/Cyto13-vir complex, where the two charged N531 (Hδ22)•••E-3(Oε2)•••S545(Hγ) H-bonds (orange/cyan residues and red dotted lines) are replaced by uncharged bonds involving Q-3(Oε1).

Figures 5A, 5B:
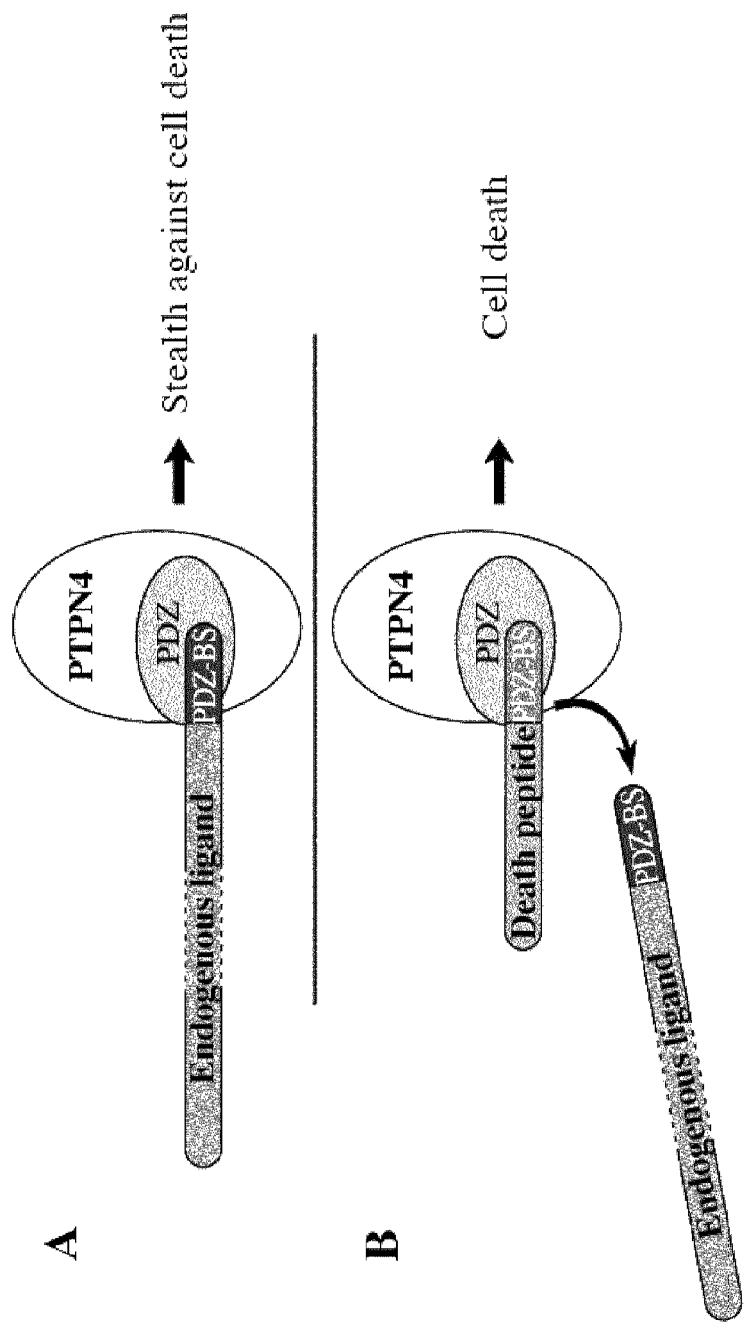

FIG. 5A-5B. Proposed mechanism of cell death triggered by death peptides. (A) In non-infected cells, the interaction of PTPN4-PDZ with its endogenous ligand protects the cell from apoptosis. (B) After infection with a pro-death RABV strain (att) or treatment with a death peptide targeting PTPN4-PDZ, cells are not protected against death because of a disruption of the interaction between PTPN4-PDZ and its endogenous ligand.

Figure 6:
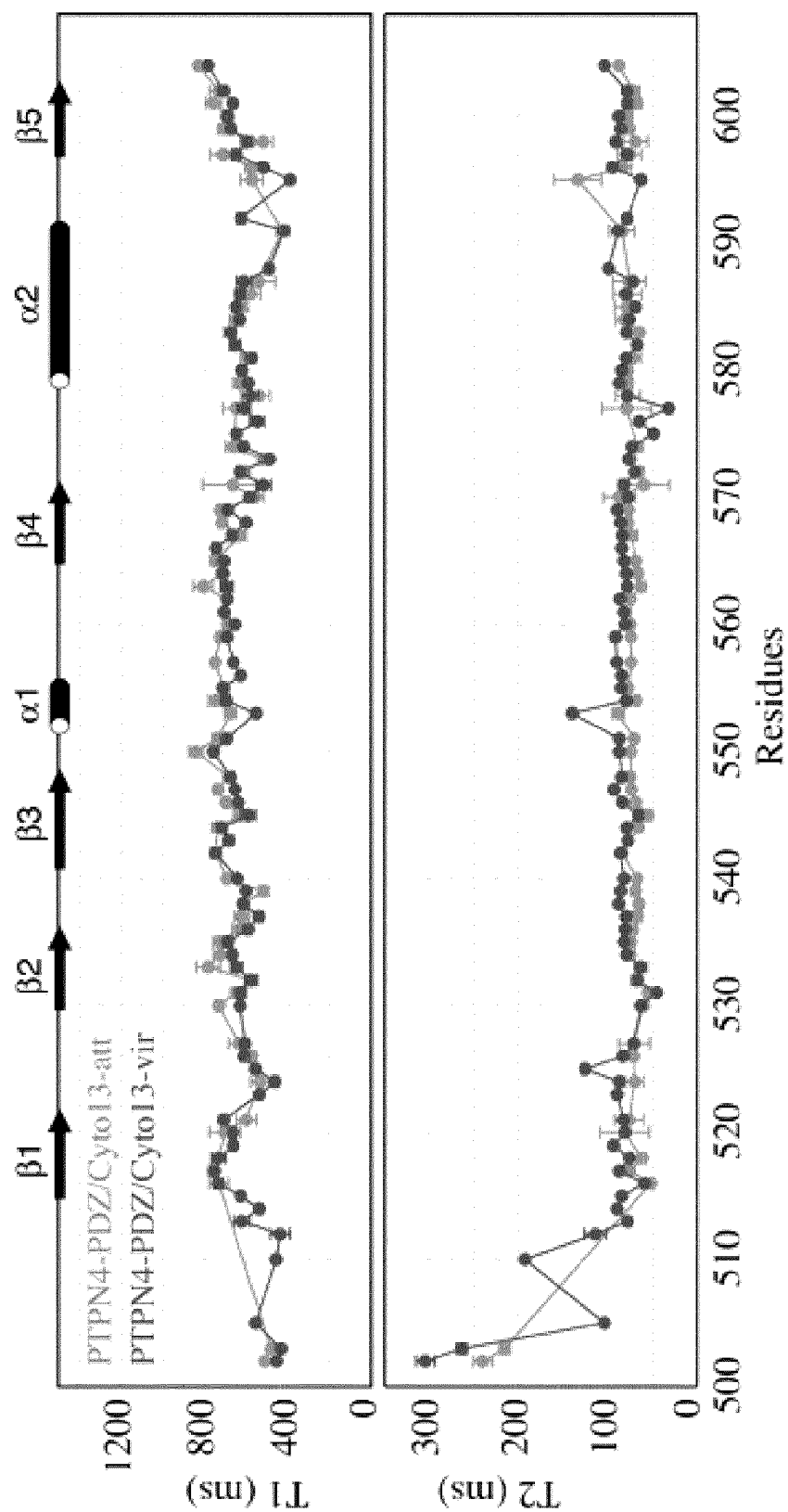

FIG. 6. Backbone dynamics of PTPN4-PDZ in complex with Cyto13-att (green) and Cyto13-vir (red) as determined by NMR $^{15}$N relaxation data. $^{15}$N longitudinal (T$_1$) and transversal (T$_2$) relaxation times, plotted in the top and bottom panel, respectively, were acquired using standard methods at 600 MHz $^1$H frequency and 25° C. (Kay et al, 1992). Secondary structure elements are indicated at the top. The isotropic rotational correlation times, estimated from the T$_1$/T$_2$ ratios of non-flexible residues, were 9.3 and 8.3 ns for the Cyto13-att and Cyto13-vir complexes, respectively. These values are in agreement with the theoretical value of ~7.9 ns expected for a globular molecule with a molecular weight of 13.1 kDa, which confirms the monomeric state of both complexes. Apart from the N-terminal arm and the S589-S594 region preceding β5, the T$_1$ and T$_2$ values are rather uniform, which denotes globular and overall rigid complexes. The internal mobility of PTPN4-PDZ was not significantly affected by the binding of Cyto13-att or Cyto13-vir, with rather unchanged T$_1$ and T$_2$ profiles. This observation indicates the formation of dynamically comparable complexes.

DETAILED DESCRIPTION OF THE INVENTION

The present application relates to the subject-matter as defined in the claims as filed and as herein described.

The application notably relates to products, which may trigger pro-apoptotic or pro-death effects on neoplastic cells and/or tissues of the human nervous system, and/or which may inhibit the effects of a neurotropic virus. The products of the application can notably be used as anti-proliferative or tumoricid agents in the treatment and/or palliation and/or prevention of neoplasms of the human nervous system, more particularly of human glioblastoma or human brain stem glioma.

The application relates to a peptide, the amino acid sequence of which comprises at least one of said SEQ ID NO: 1-13, more particularly at least one of SEQ ID NO: 1-10, 12-13, still more particularly at least one of SEQ ID NO: 1-10, even still more particularly at least one the peptides of SEQ ID NO: 1-9, even still more particularly at least one the peptides of SEQ ID NO: 1-8, even still more particularly at least one the peptides of SEQ ID NO: 1-7, even still more particularly at least one the peptides of SEQ ID NO: 1-6, even still more particularly at least one the peptides of SEQ ID NO: 1-5, even still more particularly at least one the peptides of SEQ ID NO: 1-4, even still more particularly at least one the peptides of SEQ ID NO: 1-3, even still more particularly at least one the peptides of SEQ ID NO: 1-2, even still more particularly the peptide of SEQ ID NO: 1.

As illustrated in the examples and in the figures below, said SEQ ID sequences are as follows:

```
                            (SEQ ID NO: 1)
SWESHKSGRETEV;

(SEQ ID NO: 2)
SWYERETEV;

(SEQ ID NO: 3)
SWEERETEV;

(SEQ ID NO: 4)
SWARVSKETPL;

(SEQ ID NO: 5)
SWERRETEV;

(SEQ ID NO: 6)
SWEERETEF;

(SEQ ID NO: 7)
SWEDRETEV;

(SEQ ID NO: 8)
SNRRVYKKMPSIESDV;

(SEQ ID NO: 9)
SWESHKSGGESDV;

(SEQ ID NO: 10)
LNLGNDPDRGTSI;

(SEQ ID NO: 11)
SWESHKSGGETRL;

(SEQ ID NO: 12)
SWPDRDRESIV;

(SEQ ID NO: 13)
SWRVDSKETEC.
```

The amino acid sequence of said peptide consists of less than 34 amino acids, more particularly of less than 30 amino acids, still more particularly of less than 29 amino acids, still more particularly of less than 28 amino acids, still more particularly of less than 27 amino acids, still more particularly of less than 26 amino acids, still more particularly of less than 25 amino acids, still more particularly of less than 24 amino acids, still more particularly of less than 23 amino acids, still more particularly of less than 22 amino acids, still more particularly of less than 21 amino acids, still more particularly of less than 20 amino acids, still more particularly of less than 19 amino acids, still more particularly of less than 18 amino acids, still more particularly of less than 17 amino acids.

According to an embodiment of the application, the amino acid sequence of said peptide consists of less than 16 amino acids, more particularly of less than 15 amino acids, more particularly of less than 14 amino acids.

The amino acid sequence of a peptide of the application may e.g., comprise one, two or three of said SEQ ID sequences.

When several of said SEQ ID sequences are contained in the amino acid sequence of a peptide of the application, said SEQ ID sequences can be the same or can different from each other. They can be directly linked to each or other, or can be indirectly linked to each via a molecular linker, such as a stretch or stretches comprises a few amino acids, e.g., 3 or 4 amino acids.

According to an embodiment of the application, a peptide of the application has an affinity for the PDZ of PTPN4 that is lower than 200 microM, more particularly lower than 160 microM, more particularly lower than 130 microM, more particularly lower than 90 microM, more particularly lower than 50 microM, more particularly lower than 45 microM, more particularly lower than 40 microM, more particularly lower than 30 microM, more particularly lower than 20 microM, more particularly lower than 10 microM, more particularly lower than 5 microM, more particularly lower than 4.9 microM, more particularly lower than 4 microM, more particularly lower than 3 microM, more particularly lower than 2.6 microM, more particularly lower than 2.1 microM, more particularly lower than 2 microM, more particularly lower than 1.7 microM, more particularly lower than 1.6 microM, more particularly lower than 1.5 microM, more particularly lower than 1.4 microM, more particularly lower than 1.3 microM, more particularly lower than 1.2 microM, more particularly lower than 1.1 microM.

PTPN4 (also known as PTPMEG1) is a human non-receptor Protein Tyrosine Phosphatase (PTP) with functions in T Cell Receptor (TCR) cell signaling, learning, maintaining spatial memory and cerebellar synaptic plasticity.

PDZ (PSD-95, Discs Large, ZO-1) domains form globular structures of 80-100 amino acids organized into six beta-strands and two alpha helices creating a socket where the C terminal sequence of a partner protein can be inserted.

In the application, any means that the person of ordinary skill in the art finds appropriate to determine or measure the affinity of said peptide can be used, for example by Nuclear Magnetic Resonance (NMR) and/or Isothermal Titration calorimetry (ITC) and/or Surface Plasmonic Resonance (SPR). Preferred means comprise those which determine or measure the $K_D$, for example by NMR, e.g., as illustrated in the examples below. The higher the $K_D$ value, the lower the affinity.

TABLE 2 affinity for PTPN4-PDZ

| SEQ ID NO: | Peptide name | Sequence | Kd (microM) |
|---|---|---|---|
| 1 | Cyto8-RETEV | SWESHKSGRETEV | 1 |
| 2 | | SWYERETEV | 1.09 |
| 3 | | SWEERETEV | 1.35 |
| 4 | | SWARVSKETPL | 1.58 |
| 5 | | SWERRETEV | 2.00 |
| 6 | | SWEERETEF | 2.52 |
| 7 | | SWEDRETEV | 3.88 |
| 8 | GluN2A-16 | SNRRVYKKMPSIESDV | 42 |
| 9 | Cyto9-ESDV | SWESHKSGGESDV | 85 |
| 10 | GluD2-13 | LNLGNDPDRGTSI | 128 |
| 11 | Cyto13-att | SWESHKSGGETRL | 157 |
| 12 | | SWPDRDRESIV | — |
| 13 | | SWRVDSKETEC | — |
| 14 | Cyto13-vir | SWESHKSGGQTRL | 568 |
| 15 | EIRL-13 | SWESYRSGGEIRL | 1167 |
| 16 | DARL-13 | SWELYKSEGDARL | 1285 |
| 17 | Cyto9-Δ | SWESHKSGG | — |

Affinity measured by NMR titration (following the method described in Préhaud et al., 2010), except for peptides of SEQ ID NO: 2-3 and 5-7 (affinity measured by ITC titration).

The symbol "-" means not measured.

"1285" means one thousand two hundred and eighty-five.

"1167" means one thousand one hundred and sixty-seven.

The amino acid sequence of a peptide of the invention may consist one of said SEQ ID sequences.

A peptide of the application can be glycosylated and/or biotynylated.

A peptide of the application can be linked to a His tag (e.g., a His tag intended for purification).

A peptide of the invention can be produced by synthesis. Any method of peptide synthesis that is known to the skilled person can be used. Examples of synthesis methods, such as the Merrifield solid phase synthesis, can e.g., be found in <<Solid Phase Peptide Synthesis>> (J. M. Steward & J. D. Young, 1969, Ed. W.H. Freeman Co., San Francisco), or in <<Peptide synthesis>> (M. Bodansky et al. 1976, John Wiley & Sons, 2nd Edition). A peptide of the invention can alternatively produced by recombinant expression of the nucleic acid encoding it, e.g., from a vector of the application (cf. below).

The application also relates to an antibody, which specifically binds to a peptide of the application, and to a fragment of such an antibody, which specifically binds to a peptide of the application.

Said antibody may be of any immunoglobulin class including IgG, IgM, IgE, IgA, IgD and any subclass thereof.

Said antibody can be a polyclonal antibody or a monoclonal antibody, more particularly a monoclonal antibody. A monoclonal antibody of the application can e.g., be produced by the hybridoma technique of Kohler and Milstein (1975) Nature 256:495-497; and U.S. Pat. No. 4,376,110, the human B-cell hybridoma technique (Kosbor et al. (1983) Immunology Today 4:72; Cole et al. (1983) Proc. Natl. Acad. Sci. USA 80:2026-2030, and the EBV-hybridoma technique (Cole et al. (1985) Monoclonal Antibodies And Cancer Therapy, Alan R. Liss, Inc., pp. 77-96). Such hybridomas also are within the scope of the application. The hybridoma may be cultivated in vitro or in vivo.

Said antibody can be a recombinant antibody, more particularly a chimeric antibody, such as:
a humanized antibody, more particularly an antibody comprising the variable region of an antibody of the invention (obtainable by immunization of a mammal other than a human against at least one peptide of the application), and a constant region derived from a human antibody;

a single chain Fv (scFv), wherein the Fv of the H-chain or the L-chain is ligated with an appropriate linker.

Said fragment can e.g., be a Fv, a Fab, a F(ab')2, or a Fab/c having one Fab and a complete Fc. An antibody or antibody fragment of the application may e.g., be useful as a means to isolate and/or purify a peptide of the invention, or as a means to link a peptide of the application to another entity, moiety or biological target or to a solid support.

The application also relates to a nucleic acid coding for a peptide of the application (in accordance with the universal genetic code, taking due account of its degeneracy).

The application also relates to a nucleic acid construct, which is an expression cassette, wherein said expression cassette codes for the expression of a peptide of the invention.

The application also relates to a vector carrying a coding nucleic acid, wherein said coding nucleic acid is a nucleic acid of the application, or carrying an expression cassette, wherein said expression cassette is an expression cassette of the application Said vector is a recombinant nucleic acid vector, more particularly an expression vector.

Such an expression vector comprises an expression cassette, in which the nucleic acid to be expressed is inserted. In such a vector, the nucleic acid encoding said at least one peptide of the application can be operably linked to at least one promoter and/or at least one regulatory sequence and/or to at least one secretion or excretion signal sequence and/or at least one polyadenylation signal sequence Such a vector is notably useful for recombinantly producing said peptide (and optionally recovering it by purification and/or isolation), and may e.g., be a plasmid, a bacteriophage, a baculovirus.

Such a vector is notably useful for delivering the encoded peptide into a human organism in need thereof, more particularly to a human nervous system in need thereof, still more particularly to a human Sympathetic Nervous System (SNS) and/or to a human Central Nervous System (CNS) in need thereof, still more particularly to a human CNS in need thereof (cf. below).

Such a vector may e.g., be useful for penetrating and/or crossing the plasma membrane of a cell of said human organism (more particularly a cell of said human SNS and/or CNS, more particularly a cell of said human CNS, more particularly a cell of said human brain, more particularly a human neuron and/or a human glial cell, more particularly a human glial cell) and/or for crossing the blood-brain barrier of said human organism.

An appropriate vector can e.g., be a recombinant plasmid, recombinant Herpes Simplex Virus (HSV) vector, a recombinant adeno-associated viral (AAV) vector, a recombinant adenoviral (Ad) vector, a recombinant retroviral vector, a recombinant lentiviral (LV) vector, a recombinant pox virus vector, as well as hybrid vectors thereof (which combine components from at least two different viral vectors), and the pseudo-typed forms of said viral vectors.

The application also relates to a host cell comprising a nucleic acid of the application and/or a vector of the application. Such a host cell can be a recombinant host cell. Examples of host cells notably comprise a prokaryotic cell, such as *E. coli* or *B. subtilis*, a eukaryotic cell, such as a yeast cell (e.g., *S. cerevisiae*), a plant cell (e.g., a Tobacco cell) or an animal cell, e.g., an insect cell, a mammalian cell, a non-human mammalian cell, a human cell.

The application relates to said peptides, nucleic acids, vectors, host cells in isolated or substantially purified form.

The application also relates to said peptides, nucleic acids, vectors in a form, wherein they are linked to, or inserted into other component(s).

The resulting compound can be defined as a compound, which comprises at least one peptide of the application or at least one nucleic acid of the application or at least one vector of the application, directly or indirectly linked to, or inserted into:
- at least one neurotropic component, said at least one neurotropic component being a neurotropic peptide, a neurotropic polypeptide, a neurotropic protein, a neurotropic glycoprotein, a neurotropic antibody, a neurotropic antibody fragment or a neurotropic nucleic acid; and/or at least one component, which adds or increases a cell specificity and/or a molecular specificity; and/or at least one component, which adds or increases cell plasma membrane penetration; and/or at least one component, which adds or increases Blood-Brain Barrier (BBB) crossing; and/or at least one component, which decreases toxicity towards the human organism; and/or at least one anti-neoplastic agent.

The terms <<linked to>> and <<inserted into>> are intended according to their respective meanings in the field.

By <<linked to>>, it is generally meant that said peptide, nucleic acid or vector is linked to the structure of said at least one neurotropic component or said at least one anti-neoplastic agent, without disrupting the primary or linear composition of said at least one neurotropic component or said at least one anti-neoplastic agent. Said linkage can be achieved at any location of the structure of said at least one neurotropic component or said at least one anti-neoplastic agent that the person of ordinary skill in the art may find appropriate.

By <<inserted into>>, it is generally meant that the inserted peptide, nucleic acid or vector is introduced between structural components of said at least one neurotropic component or said at least one anti-neoplastic agent, and is herein linked to said structural components. Preferably, said insertion is such that said at least one neurotropic component or said at least one anti-neoplastic agent retains a neurotropism or an anti-neoplastic activity, respectively.

Said linkage can be a covalent linkage or a non-covalent linkage, more particularly a covalent linkage.

The application more particularly relates to a compound of the application, wherein said at least one peptide, nucleic acid or vector is directly or indirectly linked to said at least one neurotropic component or said at least one anti-neoplastic agent.

The application more particularly relates to a compound of the application, which comprises at least one peptide of the application, directly or indirectly linked to, or inserted into:

at least one neurotropic component, said at least one neurotropic component being a neurotropic peptide, a neurotropic polypeptide, a neurotropic protein, a neurotropic glycoprotein, a neurotropic antibody, a neurotropic antibody fragment or a neurotropic nucleic acid; and/or at least one anti-neoplastic agent.

Such a compound is herein referred to as <<peptide-containing compound of the application>>.

The application more particularly relates to those peptide-containing compounds of the application, wherein said at least one peptide of the application is directly or indirectly linked to, or inserted into at least one anti-neoplastic agent.

The application more particularly relates to those peptide-containing compounds of the application, wherein said at least one peptide of the application is directly or indirectly linked to at least one anti-neoplastic agent.

According to an embodiment of the application, said at least one neurotropic component is not a rabies virus G protein nor a neurotropic fragment thereof (e.g., a fragment of at least 4 amino acids (more particularly of at least 5 amino acids, more particularly of at least 6 amino acids, more particularly of at least 7 amino acids) of a rabies virus G protein, wherein said fragment has retained a tropism for human neurons). According to an embodiment of the application, said at least one neurotropic component is not a ligand of the PDZ of PTPN4, such as GluD2 or GluN2A. According to either one of said two embodiments, the amino acid sequence of said peptide can comprise SEQ ID NO: 11, said nucleic acid can be a nucleic acid coding for such a peptide, and said vector can be a vector carrying such a coding nucleic acid.

According to an embodiment of the application, said at least one neurotropic component is a rabies virus G protein or a neurotropic fragment thereof (e.g., a fragment of at least 4 amino acids (more particularly of at least 5 amino acids, more particularly of at least 6 amino acids, more particularly of at least 7 amino acids) of a rabies virus G protein, wherein said fragment has retained a tropism for human neurons). According to an embodiment of the application, said at least one neurotropic component is a ligand of the PDZ of PTPN4, such as GluD2 or GluN2A. According to either one of said two embodiments, the amino acid sequence of said peptide can comprise at least one of SEQ ID NO: 1-10, 12-13, said nucleic acid can be a nucleic acid coding for such a peptide, and said vector can be a vector carrying such a coding nucleic acid.

According to an embodiment of the application, said at least one neurotropic component is:
a Cell-Penetrating Peptide (CPP), more particularly a polycationic CPP or an amphipathic CPP, for example TAT or Pep-1;
transferrin (e.g., transferrin linked to said peptide or nucleic acid via at least one polycation, wherein said at least one polycation can e.g., be is a cationic polymer, such as a lipopolyamine polymer, a polyamidoamine polymer, a cationic polymer polyethylenimine (PEI);
a transferrin receptor antibody, or Fab, F(ab')2, or Fv fragment thereof;
cationized albumin Said at least one polycation can e.g., be a cationic polymer, such as a lipopolyamine polymer, a polyamidoamine polymer, a cationic polymer polyethylenimine (PEI)

The application also relates to a compound of the application that comprises at least one peptide, nucleic acid or vector of the application, for its use in the treatment of a neoplasm of the human nervous system, wherein said compound carries said peptide, nucleic acid or vector through the blood-brain barrier.

According to an embodiment of the application, said at least one anti-neoplastic agent is an alkylating agent, an antimetabolite, an anthracycline, a plant alkaloid or a topoisomerase inhibitor. According to an embodiment of the application, a compound of the application has an affinity for the PDZ of PTPN4 that is lower than 200 microM, more particularly lower than 160 microM, more particularly lower than 130 microM, more particularly lower than 90 microM, more particularly lower than 50 microM, more particularly lower than 45 microM, more particularly lower than 40 microM, more particularly lower than 30 microM, more particularly lower than 20 microM, more particularly lower than 10 microM, more particularly lower than 5 microM, more particularly lower than 4.9 microM, more particularly lower than 4 microM, more particularly lower than 3 microM, more particularly lower than 2.6 microM, more particularly lower than 2.1 microM, more particularly lower than 2 microM, more particularly lower than 1.7 microM, more particularly lower than 1.6 microM, more particularly lower than 1.5 microM, more particularly lower than 1.4 microM, more particularly lower than 1.3 microM, more particularly lower than 1.2 microM, more particularly lower than 1.1 microM.

In the application, any means that the person of ordinary skill in the art finds appropriate to determine or measure the affinity of said peptide can be used, for example by Nuclear Magnetic Resonance (NMR) and/or Isothermal Titration calorimetry (ITC) and/or Surface Plasmonic Resonance (SPR). Preferred means comprise those which determine or measure the $K_D$, for example by NMR, e.g., as illustrated in the examples below. The higher the $K_D$ value, the lower the affinity.

The application also relates to nanoparticles and liposomes.

Said peptide, nucleic acid, vector, host cell or compound of the application can be contained in and/or on nanoparticles.

Said peptide, nucleic acid, vector, host cell or compound of the application can be contained in and/or on a liposome, e.g., it can be encapsulated inside a liposome or associated to a liposome delivery system. Said liposome can e.g., be a cationic liposome, a pegylated liposome. Said liposome can be loaded with nanoparticles.

The nanoparticle and/or liposome formulation of the peptide, nucleic acid, vector, host cell or compound of the application is notably useful for improved crossing of the blood-brain barrier and/or for protection against serum degradation.

The application relates to said nanoparticles and to said liposomes.

The application also relates to a composition, comprising:
at least one product, which is a peptide, a nucleic acid, a vector, a host cell, a compound or a liposome or nanoparticle of the application,
optionally at least one anti-neoplastic agent,
optionally at least one physiologically acceptable vehicle.
Said composition can e.g., be a pharmaceutical composition, a medicament or a drug.

Said at least one anti-neoplastic agent can e.g., be an alkylating agent, an antimetabolite, an anthracycline, a plant alkaloid or a topoisomerase inhibitor.

The composition of the invention may further comprise at least one pharmaceutically and/or physiologically acceptable vehicle (diluent, excipient, additive, pH adjuster, emulsifier or dispersing agent, preservative, surfactant, gelling agent, as well as buffering and other stabilizing and solubilizing agent, etc.). The composition of the invention can for example be a liquid solution, suspension, emulsion, tablet, pill, capsule, sustained release formulation, or powder. Preferably, it is formulated under a form suitable for parenteral administration. The composition of the invention can be a non-immunogenic pharmaceutical composition or drug, or an immunogenic pharmaceutical composition or drug, for example a vaccine. Any administration mode that the skilled person may find appropriate is encompassed by the present invention. Depending on how the product of the invention is formulated, it can administered by parenteral or enteral (e.g., oral) administration, preferably by parenteral administration, more preferably by parenteral injection.

The application also relates to a method of treatment of a subject, more particularly of a human being, in need thereof, which comprises administering to said subject or human being at least one peptide, nucleic acid, vector, host cell, compound, liposome or nanoparticle of the application as above-described.

The application also relates to a method of producing a pharmaceutical composition, which comprises formulating a peptide, nucleic acid, vector, host cell, compound or liposome or nanoparticle of the application with at least one pharmaceutically physiologically acceptable vehicle, carrier or diluent.

A peptide, nucleic acid, vector, host cell, compound, liposome or nanoparticle of the application is notably useful in the treatment and/or palliation and/or prevention (e.g., by administration to a human in need thereof) of a disease, disorder or condition involving an insufficient cell degeneration of the human nervous system, more particularly a disease, disorder or condition involving an insufficient cell degeneration of the Sympathetic Nervous System (SNS) and/or a disease, disorder or condition involving an insufficient cell degeneration of the Central Nervous System (CNS), more particularly a disease, disorder or condition involving an insufficient cell degeneration of the CNS, even still more particularly a disease, disorder or condition involving an insufficient cell degeneration of the brain, even still more particularly a disease, disorder or condition involving an insufficient cell degeneration of human neurons and/or of human glial cells. Such a disease, disorder or condition notably comprises a disease, disorder or condition, which involves the presence or spreading of undesired cells, such as:

tumor or neoplastic cells, or infected cells, more particularly virally-infected cells (e.g., infection by a neurotropic virus, such as rabies virus, HSV-1 or an influenza virus).

A peptide, nucleic acid, vector, host cell, compound, liposome or nanoparticle of the application is useful in stimulating the apoptosis and/or the membrane rupture of human nervous system cells, more particularly of cells of the human SNS and/or human CNS, more particularly of cells of the human CNS, more particularly of cells of the human brain, more particularly of human neurons and/or human glial cells, more particularly of human glial cells.

A peptide, nucleic acid, vector, host cell, compound, liposome or nanoparticle of the application is notably useful in stimulating the apoptosis and/or the membrane rupture of such human cells, when said human cells are dividing cells.

Such dividing cells notably comprise tumor or neoplastic cells.

The tumor or neoplasm is a tumor or neoplasm, which affects the human nervous system either as a primary tumor or neoplasm or as a secondary tumor or neoplasm, more particularly as a primary tumor or neoplasm. The tumor or neoplasm can e.g., be a solid tumor.

Hence, a peptide, nucleic acid, vector, host cell, compound, liposome or nanoparticle of the application is useful as an active principle in a composition intended for the treatment and/or palliation and/or prevention of tumor or neoplastic cells of the human nervous system, more particularly of the human SNS and/or CNS, more particularly of the human CNS, more particularly of the human brain, more particularly of human neurons and/or human glial cells, more particularly of human glial cells.

Said tumor or neoplastic cells can e.g., be malignant or pre-malignant or potentially malignant cells, more particularly malignant cells.

Illustrative tumor or neoplastic cells of the human SNS notably comprise neuroblastoma cells.

Illustrative tumor or neoplastic cells of the human CNS notably comprise glioblastoma cells (e.g., glioblastoma multiforme cells), oligodendroglioma cells, brain stem glioma ells, more particularly glioblastoma cells.

Said disease, disorder or condition involving an insufficient cell degeneration of the SNS can be an extracranial solid tumor, such as a neuroblastoma.

Said disease, disorder or condition involving an insufficient cell degeneration of the CNS can e.g., be an intracranial solid tumor, such as a glioblastoma.

A peptide, nucleic acid, vector, host cell, compound, liposome or nanoparticle of the application can also be useful as an active principle in a composition intended for the treatment and/or palliation and/or prevention of an infection of a human being by a neurotropic virus, such as rabies virus, HSV-1 or an influenza virus, more particularly an infection of the human nervous system (more particularly the SNS and/or the CNS, more particularly the CNS, still more particularly the brain). Indeed, a peptide, nucleic acid, vector, host cell, compound, liposome or nanoparticle of the application may e.g., compete with a neurotropic virus and inhibit its effects.

A peptide, nucleic acid, vector, host cell, compound, liposome or nanoparticle of the application can be immunogenic or non-immunogenic. The main mode of action of such a compound is a non-immunogenic one, according to which it competes with the virus. Hence, such a peptide, nucleic acid, vector, host cell, compound, liposome or nanoparticle of the application can be comprised as an active principle in a pharmaceutical composition which is a non-immunogenic pharmaceutical composition. In such a composition, said compound is non-immunogenic.

If desired, such a peptide, nucleic acid, vector, host cell, compound, liposome or nanoparticle of the application may nevertheless be chosen to be immunogenic or may be rendered immunogenic (e.g., by linking or otherwise associating it with an immunogenicity enhancer or adjuvant). Alternatively, such a peptide, nucleic acid, vector, host cell, compound, liposome or nanoparticle of the application may be non-immunogenic and be nevertheless used for simultaneous or differed administration with another active principle that is an immunogenic one.

Therefore, such a peptide, nucleic acid, vector, host cell, compound, liposome or nanoparticle of the application may be comprised as an active principle in a composition, more particularly a pharmaceutical composition, which is an immunogenic composition or a vaccine. In such a composition, said compound can be immunogenic or can be non-immunogenic.

The application also relates to a complex comprising:
at least one PTPN4 or at least one PDZ-containing fragment thereof, coupled by non-covalent linkage to
at least one peptide of the application or to at least one peptide-containing compound of the application.

In the application, said complex is being herein referred to as <<PTPN4 complex of the application>>.

The application also relates to a crystal comprising:
at least one peptide of the application, or
at least one peptide-containing compound of the application, more particularly at least one peptide-containing compound of the application, wherein said at least one peptide of the application is directly or indirectly linked to, or inserted into at least one anti-neoplastic agent, or
at least one PTPN4 complex of the application, or
at least one antibody or antibody fragment of the application.

The atomic coordinates and structure factors have been deposited in the Brookhaven Protein Data Bank under:
accession code 3NFK for the PTPN4-PDZ/Cyto13-att complex (Cyto13-att=SEQ ID NO: 11),
accession code 3NFL for the PTPN4-PDZ/GluN2A-16 complex (GluN2A-16=SEQ ID NO: 8).

The person ordinary skill in the art can also refer to the guidelines and information available from the worldwide Protein Data Bank (wwPDB), more particularly the "Protein Data Bank Contents Guide: Atomic coordinate Entry Format Description" e.g., version 3.20, and the wwPDB Processing Procedures and Policies Document March 2009, e.g., version 2.3. (http://www.wwpdb.org/docs.html).

A crystal of the application may further comprise molecule(s) originating from the solution in which the complex has been crystallized, such as molecules of:
- solvents (e.g., organic solvents such as methyl-2-pentanediol-2,4 (MPD), ethanol, methanol, isopropanol, acetone, dioxane, 2-propanol, acetonitrile, DMSO, ethylene glycol, n-propanol, tertiary butanol, ethyl acetate, hexane-1,6-diol, 1,3-propanediol, 1,4-butanediol, 1-propanol, 2,2,2-trifluoroethanol, chloroform, DMF, ethylenediol, hexane-2,5-diol, hexylene-glycol, N,N-bis(2-hydroxymethyl)-2-aminomethane, N-lauryl-N,N-dimethylamine-N-oxide, n-octyl-2-hydroxyethylsulfoxide, pyridine, saturated octanetriol, sec-butanol, triethanolamine-HCl),
- salts (e.g., magnesium salts such as $MgCl_2$, ammonium salts, calcium salts, lithium salts, potassium salts, sodium salts or other salts),
- long-chain polymers (e.g., PEG such as PEG 4000, PEG 6000, PEG 8000; PEG 3350; polygalacturonic acid; polyvinylpyrrolidone),
- buffers (e.g., a TRIS buffer such as the 0.1M Tris buffer pH 8.5),
- precipitating agents,
- water,
- small binding proteins;
- impurity.

The application also relates to a computer device or computer device system comprising:
- storage means storing atomic coordinates; and
- a software for identifying or developing ligands based on said atomic coordinates.

Said atomic coordinates advantageously are at least the atomic coordinates of a peptide or complex of the application.

Said computer system device may further comprise means displaying molecular representations (and/or 3D conformation) and/or means for calculating binding affinities. For example, said computer system device may further comprise:
- means displaying representations (and/or the 3D conformation) of:
  - candidate ligands, which may bind to the PDZ of PTPN4, and
  - PTPN4 or PDZ-containing fragment thereof;
and/or
- processing means for calculating binding affinities between:
  - said candidate ligands, and
  - said PTPN4 or PDZ-containing fragment thereof The application also relates to a solid support, onto which at least one peptide, nucleic acid, vector, host cell, antibody, compound, liposome or nanoparticle, or complex of the application is bound, by covalent or non-covalent linkage.

Said solid support may e.g., be a solid support suitable for the screening of organic molecules, preferably a chip.

Said solid support can e.g., be an essentially polymeric material, or an essentially plastic material, notably a polystyrene material, or a glass material, or a silicon material, or a magnetic material, or a non-magnetic material.

Said solid support may more particularly be a plastic plate, notably a polystyrene plaque, comprising several wells suitable for molecular binding analysis, such as a protein titration or microtitration plate, e.g., an ELISA plate.

Said solid support may more particularly be microbeads, e.g., magnetic microbeads or non-magnetic microbeads, more particularly microbeads suitable for microtitration, e.g., according to a Luminex® technology (12212 Technology Blvd.; Austin, Tex. 78727; United States of America).

Said at least one peptide, nucleic acid, vector, host cell, antibody, compound, liposome or nanoparticle, or complex of the application can be directly bound to said solid support, or indirectly bound thereto via at least one capture or linking agent that is attached to said solid support. Said at least one capture or linking agent may comprise a portion that is attached to said solid support and a portion that comprises a ligand, which specifically binds to said at least one peptide, nucleic acid, vector, host cell, antibody, compound, liposome or nanoparticle, or complex of the application. Such a ligand can e.g., an antibody, a monoclonal antibody, or a fragment thereof which has retained said binding specificity (e.g., a Fv, Fab or F(ab')2 fragment thereof, or a polypeptide containing one or several CDR thereof).

The application also relates to a kit, comprising at least one solid support or chip of the application.

In the application, unless specified otherwise or unless a context dictates otherwise, all the terms have their ordinary meaning in the relevant field(s).

The term "comprising", which is synonymous with "including" or "containing", is open-ended, and does not exclude additional, unrecited element(s), ingredient(s) or method step(s), whereas the term "consisting of" is a closed term, which excludes any additional element, step, or ingredient which is not explicitly recited.

The term "essentially consisting of" is a partially open term, which does not exclude additional, unrecited element(s), step(s), or ingredient(s), as long as these additional element(s), step(s) or ingredient(s) do not materially affect the basic and novel properties of the invention.

The term "comprising" (or "comprise(s)") hence includes the term "consisting of" ("consist(s) of"), as well as the term "essentially consisting of" ("essentially consist(s) of"). Accordingly, the term "comprising" (or "comprise(s)") is, in the present application, meant as more particularly encompassing the term "consisting of" ("consist(s) of"), and the term "essentially consisting of" ("essentially consist(s) of").

In the application, the term "at least x" relating to a set or group of n elements (wherein x is different from zero, and n is a number that is higher than x), explicitly encompasses each value, which is comprises between x and n. For example, the term "at least one" relating to a group or set of six elements explicitly encompasses one, two, three, four, five and six of said elements, as well as at least two, at least three, at least four, at least five of said elements.

In an attempt to help the reader of the present application, the description has been separated in various paragraphs or sections. These separations should not be considered as disconnecting the substance of a paragraph or section from the substance of another paragraph or section. To the contrary, the present description encompasses all the combinations of the various sections, paragraphs and sentences that can be contemplated.

Each of the relevant disclosures of all references cited herein is specifically incorporated by reference. The following examples are offered by way of illustration, and not by way of limitation.

EXAMPLES

Example 1

Experimental Procedures

Cells

Human grade III U373MG astrocytoma cells (ATCC, HTB 17) were propagated as previously described (Lafon et al, 2005).

ATCC is American Type Culture Collection [10801 University Blvd.; Manassas, Va. 20110-2209; United States of America].

Detection of Synthetic Peptide Entry and Cell Death

Peptides were conjugated to the HIV-1 Tat domain and labelled with a FITC molecule as previously described (Préhaud et al, 2010). U373MG cells (250,000 cells per well in 1 mL culture medium) were treated with FITC-conjugated peptides (25 microM). Three hours post-treatment, cells were detached by trypsin treatment, washed in phosphate buffer (SPB) $Ca^{2+}Mg^{2+}$, and assayed for peptide entry and cell death. Membrane permeation, a marker of cell death, was measured by detecting the passage of PI (R&D system Annexin V kit). Cells were analyzed by flow cytometry. 30,000 cells were sampled for each analysis. Results were given as percentages of dead cells among peptide loaded cells.

Sample Preparation

Peptides were synthesized in solid phase using an Fmoc strategy (Covalab).

Expression and purification of PTPN4-PDZ samples for NMR and crystallogenesis were performed as follows. PTPN4-PDZ (also know as PTPMEG1) is known to the person of average skill in the art and is for example available under UniProtKB: P29074. PTPN4-PDZ (residues G499-N604, G499 being a non-native residue due to the TEV cleavage site) was encoded as an N-terminal glutathione S-transferase (GST)-tagged protein in the pDEST15 expression plasmid (Gateway System, Invitrogen). The vector was used to transform *Escherichia coli* BL21 (DE3) star (Invitrogen). Cells were grown in a 1.6 L bioreactor of either stable isotopically labeled M9 minimal medium containing 1.0 g/L $15NH_4Cl$ as the sole nitrogen source for NMR experiments or high-density medium. Protein expression was induced at $OD_{600\ nm}$ 2.5 with 0.5 mM IPTG at 30° C. for 3 h. Harvested cells were resuspended in buffer A (50 mM Tris-HCl, 150 mM NaCl, pH7.5) with 2 mM β-mercaptoethanol and a protease inhibitor cocktail (Roche), and then disrupted in a French press. Clarified cell lysate was then loaded on a GST column (GSTrap HP, GE) equilibrated with buffer A containing 2 mM dithiothreitol (DTT). The GST tag was cleaved by the TEV protease (1% M/M), which was directly injected on the column, overnight at 4° C. The samples containing PTPN4-PDZ were pooled and concentrated to 1.0 ml, and then loaded onto a size exclusion column (Sephacryl S-100 HP 16/60, GE) equilibrated with buffer A containing 2 mM DTT. All purification steps were performed at 4° C. and in the presence of a protease inhibitor cocktail (Roche). The size, purity, and sequence of the PTPN4-PDZ samples were checked by SDS-PAGE, mass spectroscopy, and microsequencing using Edman degradation. Protein concentrations were estimated from the absorbance at 280 nm, assuming a calculated extinction coefficient of 1850 $M^{-1}$ $cm^{-1}$ as determined by amino acid analysis of aliquots from a purified PTPN4-PDZ solution of known absorbance, after 6 N HCl hydrolysis for 24 h at 110° C. $D_2O$ (12%) was added to NMR samples.

Crystallization, Data Collection, and Structure Determination

Initial crystallization screening was carried out by the vapor diffusion method using a Cartesian™ nanoliter dispensing system (Santarsiero et al, 2002). Sitting drops containing 200 nL of protein complex (6 mg/mL) and 200 nL of the crystallization solution were equilibrated against 150 mL of the buffer solution in Greiner plates. Screening trials (576 conditions) were performed using commercially available sparse-matrix kits. The crystallization conditions were reproduced and optimized using crystallization solutions generated by the Matrix Maker automated formulation system from Emerald BioSystems.

Crystals were grown at 18° C. using the sitting drop vapor diffusion method. The protein solution was mixed with crystallization buffer and equilibrated against a reservoir of crystallization buffer. The Cyto13-att and GluN2A-16 peptides (SEQ ID NO: 11 and 8, respectively) used for PDZ-peptide co-crystallization were added in excess to form more than 95% complex. The crystallization conditions and mixing ratios of protein to crystallization buffer are given in Table 3. Crystals were cryo-cooled by plunging them into liquid nitrogen, and X-ray data were collected at 100 K using a nitrogen stream. When appropriate, the crystals were transferred first into a cryoprotectant solution consisting of crystallization condition plus glycerol (Table 3) before being cryo-cooled. X-ray data were collected for the PTPN4-PDZ/Cyto13-att complex on beamline Proxima I at the Soleil synchrotron (St. Aubin, France); diffraction images were measured with a rotation of 1° per image at a wavelength of 0.918 Å (Table 3). X-ray data were collected for the PTPN4-PDZ/GluN2A-16 complex on beamline PX1 of the Swiss Light Source for the PTPN4-PDZ/GluN2A-16 complex using the high-resolution diffractometer set up; diffraction images were measured with a rotation of 0.25° per image at a wavelength of 0.9795 Å (Table 3). The data were processed with MOSFLM or XDS, SCALA, and other programs from the CCP4 suite (1994). Structures were solved by molecular replacement using PHASER (McCoy, 2007) and the atomic model of PTPN4-PDZ (PDB accession code 2VPH). The locations of the bound peptides were determined from a Fo-Fc difference electron density map. Models were rebuilt using COOT (Emsley & Cowtan, 2004), and refinement was performed using REFMAC5 (Murshudov et al, 1997) and BUSTER (Blanc et al, 2004). The overall assessment of model quality was performed using MolProbity (Lovell et al, 2003).

TABLE 3

| Crystallization conditions | | |
|---|---|---|
| | PTPN4-PDZ/cyto13-att | PTPN4-PDZ/GluN2A-16 |
| Protein Buffer | 50 mM Tris-HCl pH 7.5, 150 mM NaCl, 2 mM DTT | 50 mM Tris-HCl pH 7.5, 150 mM NaCl, 2 mM DTT |
| [Protein] (mg/ml) | 6 | 6 |
| Protein:Peptide ratio | 1:5 | 1:2 |
| Crystallization conditions | 24% PEG 1500, 20% Glycerol | 24% PEG 4000, 0.2M (NH4)$_2$SO4 |
| Protein:Precipitant ratio in crystallization drop (ml) | 1:1 | 1:1 |
| Cryo-protectant | None | 25% Glycerol |

NMR Experiments

NMR data were recorded at 298 K on a Varian Inova 600-MHz spectrometer equipped with a cryogenically cooled triple-resonance pulsed field gradient probe. NMR titration experiments to measure PTPN4-PDZ/peptide affinities were performed as previously described (Préhaud et al, 2010) using 0.16 mM $^{15}$N-labeled PTPN4-PDZ with stepwise additions of unlabeled peptides.

Data Collection and Structure Determination

Further details on X-ray data collection, processing, molecular replacement using the atomic model of PTPN4 (PDB code 2VPH), and refinement are given in Table 3. The atomic coordinates and structure factors have been deposited in the Brookhaven Protein Data Bank under accession codes 3NFK for PTPN4-PDZ/Cyto13-att and 3NFL for PTPN4-PDZ/GluN2A-16).

TABLE 4

Crystallographic and Structure Refinement Statistics

|  | PTPN4/Cyto13-att | PTPN4/GluN2A16 |
|---|---|---|
| Crystal Form |  |  |
| Space group | P2$_1$2$_1$2$_1$ | P2$_1$2$_1$2$_1$ |
| Unit cell (Å, °) | 53.43, 53.-70, 81.80 90, 90, 90 | 51.58, 51.68, 190.90 90, 90, 90 |
| Molecules per asymmetric unit | 2 | 4 |
| Data Collection[a] |  |  |
| Resolution Range (Å) | 34.37-1.43 (1.51-1.43) | 95.45-1.91 (2.01-1.91) |
| Number of unique reflections | 42795 | 38978 (4287) |
| Completeness (%) | 96.7 (96.7) | 96.1 (74.7) |
| Multiplicity | 3.5 (3.6) | 4.2 (2.1) |
| $R_{merge}$ (%)[b] | 6.8 (30.1) | 4.3 (30.9) |
| <I/σ (I)> | 10.9 (4.2) | 21.1 (2.0) |
| Refinement |  |  |
| R factor (%)[c] | 19.2 | 21.7 |
| $R_{free}$ (%)[d] | 20.4 | 24.7 |
| Rmsd bond length (Å) (angle [°]) | 0.010 (1.41) | 0.010 (1.17) |
| Ramachandran Plot[e] |  |  |
| Most favored (%) | 100 | 99.16 |
| Additional allowed (%) | 0 | 0.84 |
| Outliers (%) | 0 | 0 |
| PDB entry | 3NFK | 3NFL |

Figures 2A, 2B, 2C:
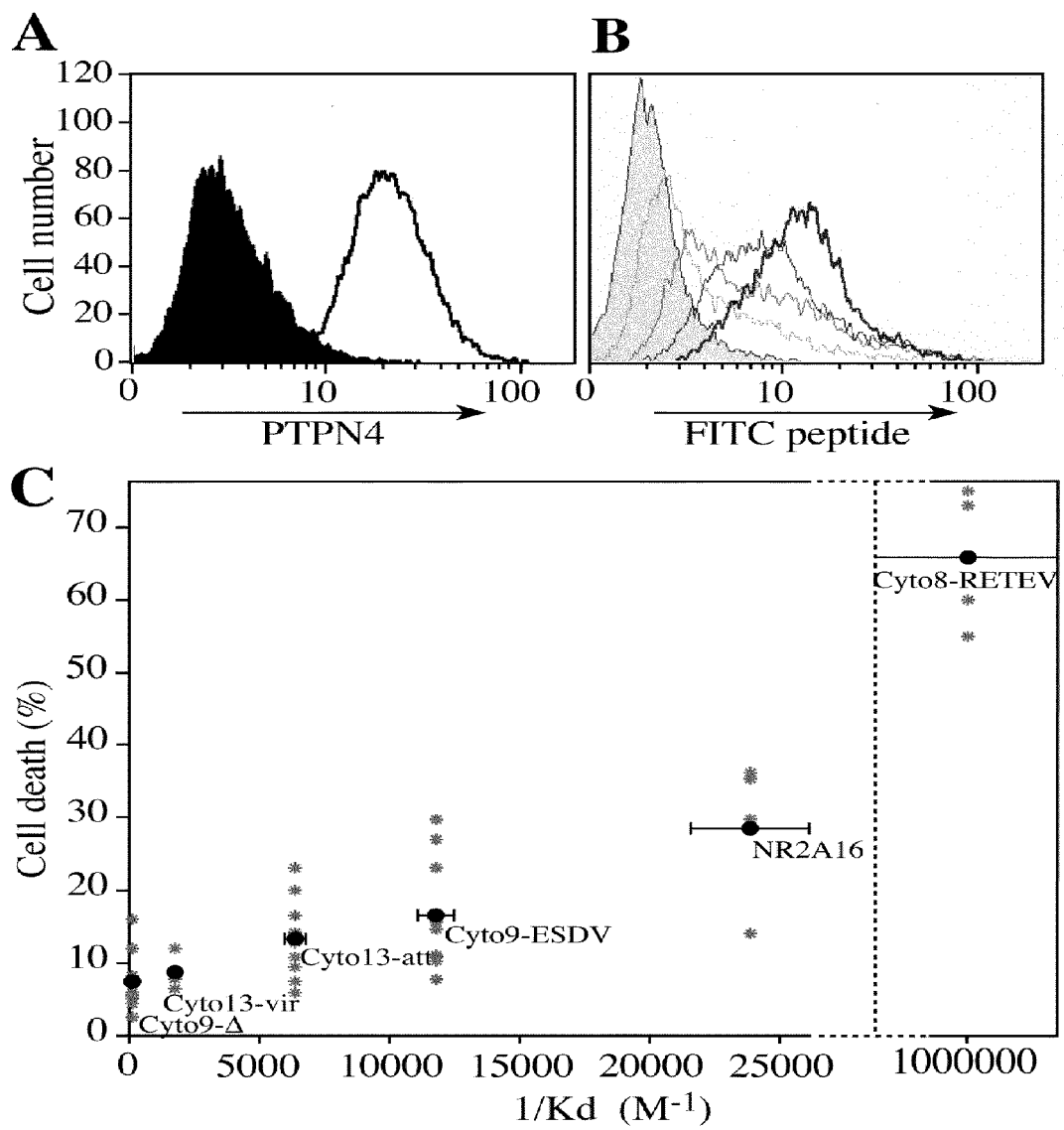
FIGS. 2A-2C. Induction of death in U373MG astrocytoma cells is related to peptide affinity for PTPN4-PDZ. (A) U373 MG cells express PTPN4. The cells were treated with primary PTPN4 antibody followed by FITC-conjugated secondary antibody (line) or with secondary antibody alone (grey histogram). Specific index of fluorescence (SFI)=4. SFI>1.25 was considered positive. (B) Kinetics of peptide loading. U373MG cells were treated with 25 μM FITC-TAT-Cyto9-Δ. Peptide loading in non-permeabilized live cells was analyzed by flow cytometry 10, 20, 40, 60, 120, and 180 min after treatment. The grey histogram corresponds to the background fluorescence of untreated cells. The SFI was 1.5, 1.6, 1.8, 1.7, 2.4, and 8.5, respectively. (C) Cell death was induced by a 3 h peptide treatment in n independent experiments: Cyto9-Δ (n=9), Cyto13-vir (n=4), Cyto13-att (n=10), Cyto9-ESDV (n=10), GluN2A-16 (n=4) and Cyto8-RETEV (n=4) [SEQ ID NO: 17, 14, 11, 9, 8 and 1, respectively]. Cell death (% of dead cells among cells having loaded the peptide, blue stars*) is plotted against 1/Kd values.

[a]Values in parentheses refer to statistics in the highest bin.
[b]$R_{merge}$ = Σ|(I − <I>)/Σ (I).
[c]R factor = Σ|F$_{obs}$ − F$_{calc}$|/Σ F$_{obs}$
[d]R$_{free}$ was calculated with 5% of the data excluded from the refinement.
[e]Categories were defined by MolProbity Results Peptide affinity for PTPN4-PDZ and killing efficiency
We synthesized nine peptides:
four viral peptides: Cyto13-att (SEQ ID NO: 11), Cyto13-vir (SEQ ID NO: 14), EIRL-13 (SEQ ID NO: 15), DARL-13 (SEQ ID NO: 16),
the C-terminal sequences of two already known endogenous partners of PTPN4-PDZ: GluN2A-16 (SEQ ID NO: 8) and GluD2-13 (SEQ ID NO: 10),
a chimeric peptide encoding the PDZ-BS of GluN2A and the core of Cyto-att (Cyto9-ESDV; SEQ ID NO: 9),
Cyto13-att truncated from its PDZ-BS (Cyto9-4; SEQ ID NO: 17) and
the optimized peptide sequence Cyto8-RETEV (SEQ ID NO: 1).
The affinity of these peptides for PTPN4-PDZ was measured by NMR titration (FIG. 1). The killing efficiency of five Tat-conjugated peptides exhibiting various affinities for PTPN4-PDZ was estimated in U373 MG, a human glioblastoma cell line expressing PTPN4 (FIG. 2A).

After a 3 h exposure of U373MG to the peptides, a period of time that allows for maximal peptide entry (FIG. 2B), the induction of cell death was assayed by propidium iodide (PI) assay. All peptides displayed a similar capacity to enter the cells. Cyto9-Δ, the peptide which lacks the last four amino acids does not interact with PTPN4-PDZ since it lacks the PDZ-BS, induced a low level of death (7%); Cyto13-vir, which has a low affinity for PTPN4-PDZ (dissociation constant, Kd, of 560 μM), did not increase cell death above this baseline level (8%), whereas Cyto13-att (Kd=160 μM) triggered the death of more than 14% of cells (Prehaud et al., 2010). Therefore, the single Q>E mutation increases the binding affinity enough to significantly promote the death of glioblastoma cells by the cell-penetrating peptide. GluN2A-16, which binds PTPN4-PDZ in vitro with higher affinity (Kd=42 μM) triggered death in 29% of the glioblastoma cell population, a two-fold increase compared to Cyto13-att. To test whether residues upstream of position −3 impact affinity and function, the chimeric peptide Cyto9-ESDV was studied. The Kd value of Cyto9-ESDV for PTPN4-PDZ increased from 42 μM, the Kd of the parent peptide GluN2A-16, to 85 μM and the capacity to trigger death decreased by half Glioblastoma were also treated with the antitumoral agent shepherdin. Shepherdin is a cell permeable peptidomimetic that triggers tumors cell death by antagonizing the complex formed between the antiapoptotic and mitotic regulator survivin and the molecular chaperone HSP90 (Plescia et al., 2005). A 5 h treatment with 50 μM shepherdin induces glioblastoma death in a range similar to those obtained with Cyto13-att (data not shown).

Altogether, these data indicate that the affinity of the last 4 residues of a putative PDZ-BS for PTPN4-PDZ is a critical determinant for the induction of cell death. We established that the killing efficiency of the peptide is closely reflected by their respective affinity for the PTPN4-PDZ. According to the scenario depicted in FIG. 5, it appears that a threshold value in the affinity of the competing peptide for the PDZ domain of PTPN4 has to be reached, corresponding roughly to a Kd lower than 200 μM.

Crystal Structures of PTPN4-PDZ in Complex with the Peptides

PTPN4-PDZ/Cyto13-att Structure

Two molecules in the asymmetric unit are disulfide-bonded. Each molecule corresponds to the complex formed by PTPN4-PDZ (chains A and B) and the Cyto13-att peptide (chains C and D). In order to check the oligomeric state of the complex, NMR experiments (FIG. 5) and analytical ultracentrifugation (data not shown) were performed under reducing conditions (2 mM DDT). We confirmed a stable monomeric form of the PTPN4-PDZ/Cyto13-att complex in solution, implying that the intermolecular disulfide bond is due to crystalline conditions. In one complex (chains B/D), the electron density of only five residues of Cyto13-att (chain D) was well defined, whereas, due to crystal packing in the other complex (chains A/C), all of the 13 residues of Cyto13-att in chain C were well ordered. Chains A and B superimpose very well with a Ca RMSD of 0.25 Å, indicating that crystal packing has no influence in the overall structure of the PDZ domain. The PTPN4-PDZ/Cyto13-att complex formed by the B and D chains is described below.

PTPN4-PDZ/GluN2A-16 Structure

Four molecules were found in the asymmetric unit, constituting four monomers. Each molecule corresponds to the complex formed by PTPN4-PDZ (chains A to D) and the GluN2A-16 peptide (chains E to H). Chain A is disulfide-bonded to chain D and chain B is disulfide-bonded to chain C. NMR experiments and analytical ultracentrifugation (data not shown) also confirmed that the disulfide bonds are due to the crystalline conditions. In all peptide chains, the electron density of only five of the sixteen residues was well defined in the crystal. Superimposition of all PTPN4-PDZ chains displayed a Cα RMSD of less than 0.3 Å, indicating that no crystal packing influence exists in the overall structure of the PDZ domain. Because peptide chain E does not experience any crystal contacts, we described the PTPN4-PDZ/GluN2A-16 complex formed by the A and E chains.

Structure of the PTPN4-PDZ/Viral Peptide Complex

To investigate the specificity of PTPN4-PDZ for the attenuated RABV G protein, the crystal structure of the complex formed by PTPN4-PDZ and Cyto13-att was solved by molecular replacement at 1.4 Å resolution (Table 4).

Figures 3A, 3B, 3C, 3D:
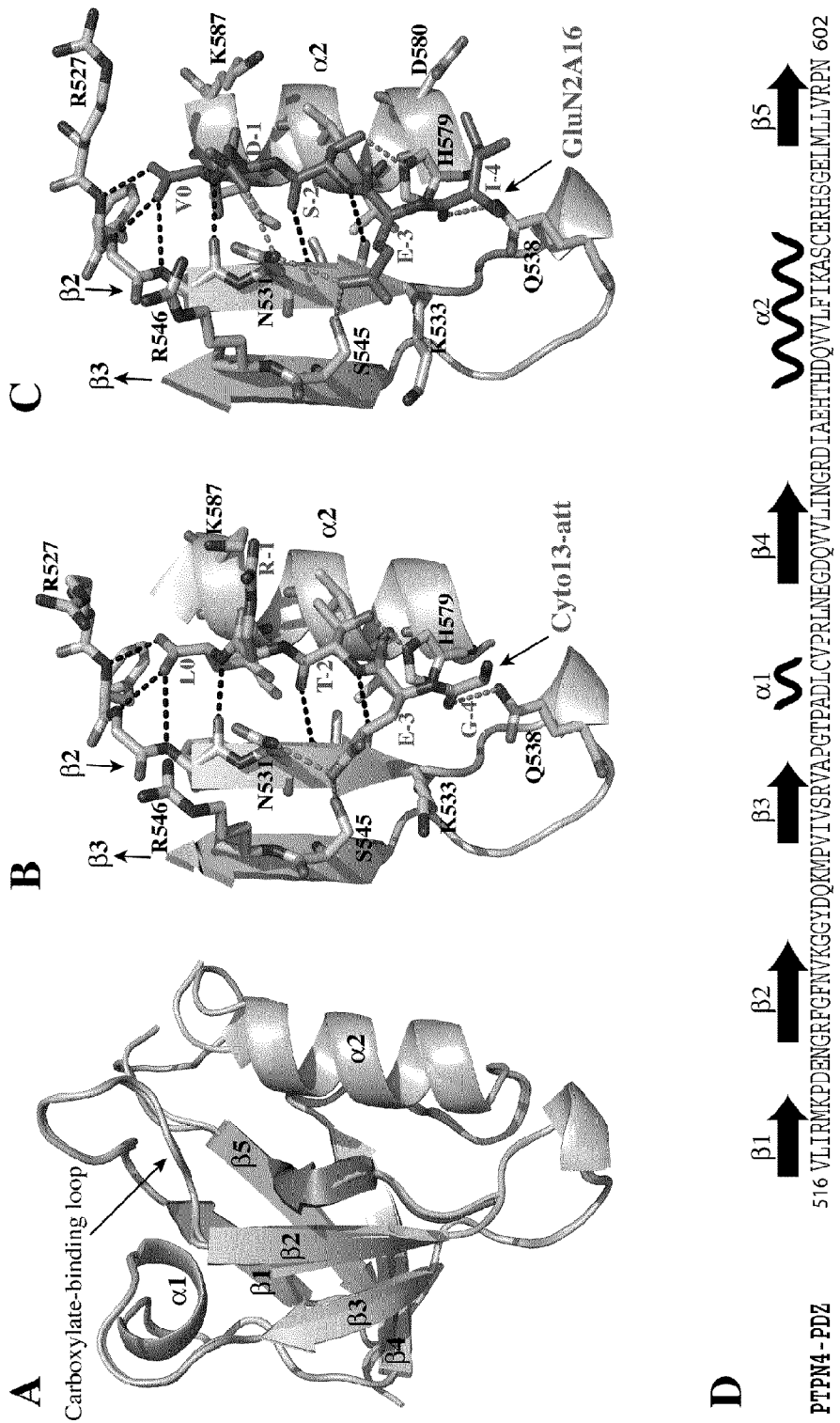

PTPN4-PDZ adopts a typical PDZ fold comprising of five β-strands and two α-helices (FIGS. 3A and 3D). Only the last five C-terminal peptide residues of Cyto13-att (-GETRL$_{COOH}$) were well ordered in the crystal, and the peptide was inserted into the PDZ binding pocket in a conventional mode (FIG. 3B).

PTPN4-PDZ possesses the interaction network specific to class I PDZ domains and recognizes the consensus peptide sequence X-S/T-X-Φ$_{COOH}$, where X is any residue and Φ is a hydrophobic residue. At position −1, the electron density beyond the Cγ atom of the R residue is not clearly assigned. This cationic side chain is completely exposed to the solvent, surrounded by positively charged residues (R527, R546, and K587), and does not contact any PTPN4-PDZ residues. Position −3 is a critical determinant of the PTPN4-PDZ/Cyto13-att interaction. The side chain carboxyl of E-3 forms a bifurcated H-bond with the hydroxyl of S545 and N531 amine group. E-3 is also strongly stabilized by hydrophobic contacts involving its Cβ-Cγ carbon chain and the long aliphatic side chain of K533 in a manner quite reminiscent of the bonding patterns observed for complexes involving PDZ domains highly structurally related to PTPN4-PDZ, the α1- and β2-syntrophin-PDZ (PDB entry 2PDZ and 2VRF, respectively). Lastly, the carbonyl oxygen of G-4 forms an H-bond with the amide nitrogen of Q538.

Though PDZ domain classification is essentially based on positions 0 and −2, numerous studies have emphasized the importance of the other positions −1, −3, and −4, crucial for PDZ/PDZ-BS interactions. Indeed as described above, E-3 is involved in an extended interaction network with residues of the PTPN4-PDZ β-sheet. In contrast, residues occupying positions −1 and −4 of Cyto13-att do not appear to be optimal for the interaction with PTPN4-PDZ (Kd=160 μM), likely accounting for the fact that the overall affinity remains rather weak for a PDZ/PDZ-BS interaction, more generally in the 1-10 μM range.

Structural Consequences of the E/Q Mutation

When affinities of the Cyto13-vir and Cyto13-att peptides for PTPN4-PDZ were compared, a 4 fold difference in Kd was noted, Q-3 having a higher Kd than E-3 (FIG. 1) (Préhaud et al., 2010). We used NMR spectroscopy to characterize a potential structure/affinity relationship that could explain this difference in affinity between the two viral peptides. First, backbone dynamics from $^{15}$N relaxation measurements revealed an overall rigid structure of PTPN4-PDZ and no detectable changes in the dynamic behavior of the two Cyto13-att and Cyto13-vir complexes (FIG. 6). In the crystal structure of the PTPN4-PDZ/Cyto13-att complex, residues N531, K533 and S545 are in contact with Cyto13-att E-3. Charged H-bonds are generally stronger than uncharged bonds. Therefore, we carefully examined the NMR chemical shifts of H-bonding amide protons (HN), which correlate with the strength of H-bonds. Surprisingly, this analysis revealed that the β2/β3/β4 canonical H-bond network in close vicinity of the E/Q mutation is locally strengthened in Cyto13-vir compared to the Cyto13-att complex (FIG. 4A, B). This fine-tuned structural rearrangement leads to a favorable energetic contribution, which partially balances the unfavorable replacement of the bifurcated and charged N531 (Hδ22) • • • E-3(Oε2) • • • S545(Hγ) H-bonds with neutral ones involving the isosteric residue Q-3. Such a compensatory effect could explain the small variation in the binding free energies of complex formation with Cyto13-vir compared to Cyto13-att, $\Delta\Delta G_0$=RT ln(Kd(Cyto13-vir)/Kd (Cyto13-att))=0.76 kcal·mol$^{-1}$, corresponding to the 4-fold difference in affinity.

In conclusion, slight modifications in the interaction network at the PDZ binding site lead to the drastic functional effect observed for the E>Q change, which is sufficient to abrogate the ability of the PDZ-BS to recruit PTPN4 and to deny the virulent strain the capacity to trigger cell death.

The vampire bat strain of RABV is another RABV strain that does not trigger apoptosis (data not shown). We analyzed the complex formed by PTPN4-PDZ with the C-terminal sequence of G protein of this strain, which is terminated by a PDZ-BS, -DARL$_{COOH}$, corresponding to a class II motif (X-Φ-X-Φ$_{COOH}$). This PDZ-BS very weakly interacts with PTPN4-PDZ with a Kd of 1285 microM, an hydrophobic residue at position −2 strongly destabilizing the complex (FIG. 1). Similar low affinity for PTPN4-PDZ has been measured for another viral C-terminal sequence (from CVS-B2C RABV strain) that encodes an I at position −2 corresponding also to a class II motif, -EIRL$_{COOH}$. Altogether these data indicate that PTPN4-PDZ interacts specifically with PDZ-BS sequences of class I.

Structure of the PTPN4-PDZ/Endogenous Peptide Complex

Two endogenous partners of PTPN4-PDZ are known: the orphan ionotropic glutamate receptor, GluD2 terminated by -RGTSI$_{COOH}$ and GluN2A terminated by -ESDV$_{COOH}$. Their terminal peptides (GluD2-13 and GluN2A-16, respectively) display affinities for PTPN4-PDZ, slightly better than the one observed for the viral peptide Cyto13-att (FIG. 1). The corresponding dissociation constants are equal to 128 μM for the former and to 42 μM for the later. In order to define the peptide positions where an improvement in the interaction could be noticed, the structure of the PTPN4 PDZ domain complexed with the more affine of these two peptides, GluN2A-16, was determined The structure of the PTPN4-PDZ/GluN2A-16 complex solved at 1.9 Å resolution was found to be very similar to the PTPN4-PDZ/Cyto13-att complex, with a RMSD of 0.21 Å (FIG. 3A,C). The overall structure of PTPN4-PDZ was not affected by peptide binding. Only the last five C-terminal residues of GluN2A-16 were resolved.

At position −1, the D side chain was well defined, in contrast to R-1 of Cyto13-att. D-1 forms an H-bond with the Q531 side chain amine group of the PDZ domain. Therefore, an acidic residue is more favorable at the penultimate position of the peptide. The nature of the residue at position −1 probably makes a significant contribution to the four-fold increase in affinity between Cyto13-att and GluN2A-16 for PTPN4-PDZ. Furthermore, the interaction network of the conserved E-3 residue was similar in both cases. I-4 was well defined in the crystal; its side chain is at a Van der Waals distance from the imidazole group of H579, and its carbonyl group is H-bonded to the amino group of the Q538 side chain. A cationic residue at position −4 is strongly preferred in highly structurally related PDZ domains. In the case of α1-syntrophin, an ionic bond occurs between K-4 of the ligand and D151 at the N-terminus of the α2 helix, an anionic position conserved in PTPN4-PDZ (D580). Lastly, in the chimeric peptide Cyto9-ESDV in which the PDZ-BS of GluN2A is inserted into the Cyto-att core, the affinity for PTPN4-PDZ dropped by a factor of 2 compared to the native GluN2A peptide. The flexibility of Cyto9-ESDV due to the presence of the glycine doublet at positions −4 and −5, and the substitution of 1-4 by a glycine residue, are likely responsible for this effect.

Tailoring Best-Suited Peptides by Structural Analysis

The identification of the most crucial determinants of ligand recognition by PTPN4-PDZ led us to conceive an optimized peptide leading to tighter interactions with the phosphatase and consequently to enhanced capacity of cell death. Considering that positions 0, −2 and −3 are involved in an extended interaction network with residues of the PTPN4-PDZ, we focused our sequence optimization on positions −1 and −4. We conceived that a long acidic residue at position −1 and cationic residue at position −4 could induce additional crucial contacts with surrounding residues of the PDZ domain, and that the PDZ-BS -RETEV$_{COOH}$ could be an optimized binding partner for PTPN4-PDZ. The chimeric peptide encoding the PDZ-BS-RETEV$_{COOH}$ with the core of Cyto13-att (Cyto8-RETEV) displays a Kd for PTPN4-PDZ that drastically decreases to 1 μM (FIG. 1). The higher affinity of Cyto8-RETEV for PTPN4-PDZ (a 160-fold increase compared to the starting viral sequence, Cyto-att, and a 40-fold increase compared to the most affine endogenous PTPN4 ligand, GluN2A-16) correlatively enhances the efficiency of the peptide to induce glioblastoma cell death: whereas GluN2A-16 triggered death in 29% of the cells, this value was enhanced by twice, reaching 66% with Cyto8-RETEV (FIG. 2C).

Discussion

We established a relationship between the affinity of peptides for PTPN4-PDZ and their ability to provoke glioblastoma cell death. The structures of PTPN4-PDZ complexed to viral and endogenous peptides allowed us to identify the structural determinants required for ligand recognition and to design a new sequence displaying a higher affinity for PTPN4-PDZ. Among the peptides tested in this example, this optimized peptide is indeed the best PTPN4-PDZ binding partner and the best inducer of cell death. These findings identify the key role of the PTPN4 PDZ domain in the mechanism controlling death in tumor cells. They strongly support the simple mechanism, depicted in FIG. 5, by which a peptide could abolish this function.

Two other members of the non-receptor phosphotyrosine phosphatase family contain either one (PTPN3) or five (PTPN13) PDZ domains. Intriguingly, they are both involved in the control of tumor cell death. PTPN13 (also termed PTP-BAS, PTPL1, PTP1E or FAP-1) is a negative regulator of CD95 (Fas)-mediated apoptosis involved in human pancreatic adenocarcinoma and colon cancer cells. The interaction between PTPN13-PDZ and the PDZ-BS of CD95 is crucial for PTPN13 activity, likely by allowing dephosphorylation of CD95 and by altering its membrane localization. In addition, the recruitment of the second PTPN13 PDZ domain by a peptide mimicking the PDZ-BS of CD95 is sufficient to promote Fas-mediated apoptosis in a colon cancer cell line. PTPN3 (also termed PTPH1) has been described as an activator of RAS oncogenesis in colorectal cancer cells. These results point out the critical role played by the interaction of phosphatase PDZ domains with the PDZ-BS of their respective ligands for controlling apoptosis or oncogenesis.

An enhanced specific abrogation of the anti-apoptotic function of PTPN4 may be obtained by targeting both the PDZ site of interaction and the catalytic center. This embodiment is under investigation. In any case, the present results show that an efficient disruption of specific PTP-PDZ/ligand interactions can be obtained via a simple optimization of candidate pro-death sequences with the help of structural design, already opening new avenues for anti-proliferative therapies.

Example 2

Eight chimeric peptides were synthetized as described in Example 1. The values of the affinity of these peptides for the PTPN4-PDZ are given in Table 2 above. U373MG cells were treated with these peptides as described in Example 1 above. These eight chimeric peptides were SWYERETEV (SEQ ID NO: 2); SWEERETEV (SEQ ID NO: 3); SWARVSKETPL (SEQ ID NO: 4); SWERRETEV (SEQ ID NO: 5); SWEERETEF (SEQ ID NO: 6); SWEDRETEV (SEQ ID NO: 7); SWPDRDRESIV (SEQ ID NO: 12); SWRVDSKETEC (SEQ ID NO: 13).

Bibliographic References (1994) The CCP4 suite: programs for protein crystallography. *Acta Crystallogr D Biol Crystallogr* 50(Pt 5): 760-763

Blanc E, Roversi P, Vonrhein C, Flensburg C, Lea S M, Bricogne G (2004) Refinement of severely incomplete structures with maximum likelihood in BUSTER-TNT. *Acta Crystallogr D Biol Crystallogr* 60(Pt 12 Pt 1): 2210-2221

Emsley P, Cowtan K (2004) Coot: model-building tools for molecular graphics. *Acta Crystallogr D Biol Crystallogr* 60(Pt 12 Pt 1): 2126-2132

Guigoni and Coulon 2002, Journal of NeuroVirology 8: 306-317.

Kay L E, Nicholson L K, Delaglio F, Bax A, Torchia D A (1992) Pulse Sequences for Removal of the Effects of Cross-Correlation between Dipolar and Chemical-Shift Anisotropy Relaxation Mechanism on the Measurement of Heteronuclear T1 and T2 Values in Proteins. *Journal of Magnetic Resonance* 97(2): 359-375

Lafon, M., Prehaud, C., Megret, F., Lafage, M., Mouillot, G., Roa, M., Moreau, P., Rouas-Freiss, N. & Carosella, E. D. Modulation of HLA-G expression in human neural cells after neurotropic viral infections. *J Virol* 79(24): 15226-15237 (2005).

Lovell S C, Davis I W, Arendall W B, 3rd, de Bakker P I, Word J M, Prisant M G, Richardson J S, Richardson D C (2003) Structure validation by Calpha geometry: phi,psi and Cbeta deviation. *Proteins* 50(3): 437-450

McCoy A J (2007) Solving structures of protein complexes by molecular replacement with Phaser. *Acta Crystallogr D Biol Crystallogr* 63(Pt 1): 32-41

Murshudov G N, Vagin A A, Dodson E J (1997) Refinement of macromolecular structures by the maximum-likelihood method. *Acta Crystallogr D Biol Crystallogr* 53(Pt 3): 240-255

Plescia, J, Salz, W, Xia, F, Pennati, M, Zaffaroni, N, Daidone, M G, Meli, M, Dohi T, Fortugno P, Nefedova Y, Gabrilovich D I, Colombo G, Alfieri D C. Rational design of shepherdin, a novel anticancer agent *Cancer Cell* 7(5):457-68 (2005).

Préhaud, C., Wolff, N., Terrien, E., Lafage, M., Megret, F., Babault, N., Cordier, F., Tan, G. S., Maitrepierre, E., Menager, P., Chopy, D., Hoos, S., England, P., Delepierre, M., Schnell, M. J., Buc, H. & Lafon, M. Attenuation of rabies virulence: takeover by the cytoplasmic domain of its envelope protein. *Sci Signal* 3(105): ra5 (2010).

Santarsiero B D, Yegian D T, Lee C C, Spraggon G, Gu J, Scheibe D, Uber D C, Cornell E W, Nordmeyer R A, Kolbe W F, Jin J, Jones A L, Jaklevic J M, Schultz P G, Stevens R C (2002) An approach to rapid protein crystallization using nanodroplets. *Journal of Applied Crystallography* 35: 278-281

WO 03/048198 published on 12 Jun. 2003 (Inv. Lafon et al.)

The invention claimed is:

1. A peptide of less than 30 amino acids comprising at least one of SEQ ID NOs: 1-3, 5 or 7, and wherein said peptide has an affinity for the PDZ of PTPN4 that is lower than 4 microM.

2. The peptide of claim 1, wherein the amino acid sequence comprises at least one of SEQ ID NOs: 1-3 or 5.

3. The peptide of claim 2, wherein the affinity for the PDZ of PTPN4 is lower than 2.6 microM.

4. The peptide of claim 1, wherein the amino acid sequence comprises at least one of SEQ ID NOs: 1, 2, or 3.

5. The peptide of claim 4, wherein the affinity for the PDZ of PTPN4 is lower than 1.5 microM.

6. The peptide of claim 1, wherein the amino acid sequence comprises SEQ ID NO : 1.

7. An isolated nucleic acid encoding the peptide of claim 1.

8. A vector comprising the nucleic acid of claim 7.

9. A non-human host cell comprising the nucleic acid of claim 7.

10. A chimeric compound comprising at least one biological molecule comprising or encoding a peptide of at least one of SEQ ID NOs: 1-3, 5, or 7, directly or indirectly linked to, or inserted into:

at least one neurotropic component, said at least one neurotropic component being a neurotropic peptide, a neurotropic polypeptide, a neurotropic protein, a neurotropic glycoprotein, a neurotropic antibody, a neurotropic antibody fragment or a neurotropic nucleic acid; and/or at least one anti-neoplastic agent.

11. A liposome or a nanoparticle, comprising at least one biological material wherein the biological material is a peptide of at least one of SEQ ID NOs: 1-3, 5, or 7, a non-human host cell or a chimeric compound comprising the peptide or a nucleic acid encoding the peptide, and a vector a comprising said nucleic acid.

12. A pharmaceutical composition, comprising:

at least one biological material wherein the biological material is the peptide of claim 1, a non-human host cell or a chimeric compound comprising the peptide or a nucleic acid encoding the peptide, a liposome or a nanoparticle comprising said peptide or the nucleic acid, and a vector comprising said nucleic acid, and at least one pharmaceutically acceptable vehicle, carrier or diluent.

13. A method of treating a malignant neoplasm of the human nervous system comprising administering to a subject in need thereof an amount of the pharmaceutical composition of claim 12.

14. The method of claim 13, wherein said nervous system is the CNS.

15. The method of claim 13, wherein said malignant neoplasm is a glioblastoma.

16. The peptide of claim 3, wherein the affinity for the PDZ of PTPN4 is lower than 2.1 microM.

17. The peptide of claim 4, wherein the affinity for the PDZ of PTPN4 is lower than 1.4 microM.

18. A non-human host cell comprising the vector of claim 8.

19. The pharmaceutical composition of claim 12, further comprising at least one anti-neoplastic agent.

20. The method of claim 14, wherein the nervous system is the brain.

* * * * *